United States Patent
Horiguchi et al.

[11] Patent Number: 6,132,212
[45] Date of Patent: Oct. 17, 2000

[54] MATERIAL AND APPARATUS FOR REMOVING DENTAL CARIES

[75] Inventors: Shoji Horiguchi, Hachioji; Masatomo Watanabe, Hashima; Tetsuo Ochiai, Nukata-gun, all of Japan

[73] Assignee: Sintobrator, Ltd., Tokyo-To, Japan

[21] Appl. No.: 09/179,447

[22] Filed: Oct. 27, 1998

[30] Foreign Application Priority Data

May 26, 1998 [JP] Japan ................... 10-144670

[51] Int. Cl.[7] ................................................. A61C 3/02
[52] U.S. Cl. ................................................. 433/88
[58] Field of Search ........................... 433/87, 88, 215

[56] References Cited

U.S. PATENT DOCUMENTS

| | | | |
|---|---|---|---|
| 1,664,369 | 3/1928 | Maurer | 433/88 |
| 2,696,049 | 12/1954 | Black | 433/88 |
| 2,759,266 | 8/1956 | Cassani | 433/88 |
| 2,814,877 | 12/1957 | Tilden | 433/88 |
| 3,344,524 | 10/1967 | Kulischenko | 433/88 |
| 3,971,136 | 7/1976 | Madsen | 433/88 |
| 4,522,597 | 6/1985 | Gallant | 433/216 |
| 4,595,365 | 6/1986 | Edel et al. | 433/88 |
| 4,696,644 | 9/1987 | Goof | 433/88 |
| 4,935,039 | 6/1990 | Miyazaki et al. | 51/309 |
| 4,950,160 | 8/1990 | Karst | 433/87 |
| 5,367,068 | 11/1994 | Lane et al. | 536/124 |
| 5,618,177 | 4/1997 | Abbott | 433/88 |
| 5,830,445 | 11/1998 | Bouillon et al. | 424/69 |

FOREIGN PATENT DOCUMENTS

| | | | |
|---|---|---|---|
| 2588182 | 10/1987 | France | 433/88 |
| 9-276292 | 10/1997 | Japan. | |

OTHER PUBLICATIONS

"New Cutting Instruments: Substituted for Conventional Rotary Cutting Instruments," S. Horiguchi et al., Japan Society for Adhesive Dentistry, AD vol. 16, No. 2, 1998, pp. 55–62.

"Selective Caries Removal with Air Abrasion," Operative Dentistry, 1998, vol. 23, pp. 236–243, S. Horiguchi et al.

*Primary Examiner*—John J. Wilson
*Attorney, Agent, or Firm*—Arent Fox Kintner Plotkin & Kahn, PLLC

[57] ABSTRACT

There is disclosed a dental caries-removing material consisting of grinding granules ejected against dental caries, or pathological issues, to remove them. The granules are obtained by pulverizing untoxic stones of seeds and have Vickers hardness values (JIS Z 1051)(Hv) of 10 to 60 and granular diameters of 40 to 160 $\mu$m. This material is prepared by pulverizing and grading stones of seeds (such as peach, plum, apricot, or Japanese apricot).

11 Claims, 1 Drawing Sheet

MATERIAL AND APPARATUS FOR REMOVING DENTAL CARIES

BACKGROUND OF THE INVENTION (1) Field of the Invention

The present invention relates to a material and apparatus for selectively removing dental caries without damaging sound dentine.

(2) Description of Related Art

Dental caries occur and progress by the following mechanism. Dentine consisting of inorganic and organic components is bated by acids produced by bacteria and thus softens. Subsequently, the remaining organic components are decomposed by bacteria, creating voids.

Dental caries would recur unless portions softened and invaded with bacteria are removed. Thus, caries must be fully removed.

Heretofore, dental caries have been cured by grinding the caries including sound dentine and forming a box-like portion to prevent the filler from coming off. In recent years, bonding resinous materials have been developed. Therefore, the filler adheres strongly to dentine. When caries are cured, it is not necessary to grind sound dental. Consequently, it has become important that caries be fully removed and sound dentine be left as much as possible.

Today, one main means for knowing the range of caries is to detect the hardness of the caries. Another main means is to know native coloration of caries. A further main means is to color the caries with a caries-detecting liquid. In particular, only the caries are dyed red. Currently, this is the most reliable method of knowing the range of caries. Removal of caries is started with removing softened caries portions sufficiently. Native colored portions due to caries or portions dyed with a caries-detecting liquid are removed with ultimate care such that sound dentine is not damaged. A round steel bar attached to a micromotor that is a rotating grounding tool has been chiefly used to remove caries.

Dental caries are so softened that the hardness on the surface-layer side cannot be measured with a Vickers hardness tester (JIS Z 1051). The hardness suddenly increases at the boundary with sound dentine and exhibits values of approximately 10 to 30 Hv. On the other hand, sound dentine shows a hardness of approximately 60 to 80 Hv.

Dental caries are removed within a narrow region of a mouth. The practitioner cannot directly view the caries, depending on the position. In this case, he or she can view the caries only with a mirror. Therefore, depending on the skill of the practitioner, the caries might be fail to be removed, in which case the caries would recur. Also, sound dentine might be excessively ground. Furthermore, long treating time and much labor are necessary even for experienced practitioner. Today, there is a demand for a method of removing only caries in a short time without depending on the skill of the practitioner.

Where grinding is done with an air turbine or a micromotor that is one of rotating grinding tools, both caries and sound dentine are ground. Therefore, only the feasible method is to select and grind only caries, depending on the skill of the practitioner. In recent years, an air-blasting apparatus using alumina grinding material has begun to be used in clinical applications. With this apparatus, sound dentine is more easily ground than caries. It is considered that it is difficult to use this apparatus to remove caries. Therefore, any method other than the method consisting of removing only caries by a practitioner with utmost care has not been developed.

We have found that only caries can be removed without grinding sound dentine by using grinding granules as material ejected from an air-blasting apparatus. The hardness of the grinding granules is not so high that sound dentine is not ground. We have proposed a caries-removing material consisting of grinding granules having a hardness equal to or less than the hardness of sound dentine, in Japanese Patent Laid-Open No. 276292/1997 (patent application Ser. No. 343730/1998).

To assure that dental caries formed in narrow regions are removed, it is desired to eject air from an ejection nozzle having a diameter of less than 1.0 mm. We have discovered that commercially available caries-removing materials such as Tyler mesh #60 are obtained by pulverizing stones of seeds of peach or apricot. If such a material is left within the mouth, little feeling of wrongness is imparted to the patient. If the patient swallows a small amount of the material, no problems take place. Furthermore, caries can be ground well with this material. However, we have discovered that the nozzle is easily clogged with this material. The stones of peach, or Tyler #60, were pulverized and granulated with micromesh. Those of the obtained granules which lie in a narrow range were used. Even in this case, the gums feel a pain, though the nozzle does not clog up.

SUMMARY OF THE INVENTION

In view of the foregoing, it is an object of the present invention to provide a caries-removing material which can be ejected, together with air, from an ejection nozzle having an inside diameter of less than 1.0 mm and which gives little pain to the gums during ejection of air.

It is another object of the invention to provide a caries-removing apparatus adapted for the caries-removing material described in the immediately preceding paragraph.

We have paid attention to pulverized stones of peach seeds that are commercially available as livestock feed #180. We have found that the problems can be solved by using pulverized seed stones having granular diameters in a certain narrow range. This caries-removing material consists of grinding particles ejected against dental caries, or pathological tissue to remove the caries. The material consists of untoxic pulverized stones of seeds and has hardness values of 10 to 60 Hv (Vickers hardness; JIS Z 1051) and granular diameters of 40 to 160 $\mu$m.

Stones of rosaceous seeds such as peach, plum, apricot, and Japanese apricot, are available as the aforementioned untoxic stones of seeds. They can grind caries well. Furthermore, they can be readily obtained as wastes from the food industry such as canned fruits, binned fruits, jams, and juices. In addition, they are seeds of fruits that have long been eaten. Since their satefy has been confirmed, their use is desirable.

Another caries-removing material in accordance with the present invention consists of grinding particles ejected against dental caries, or pathological tissue, to remove the caries, the particles being characterized in that they are granules of crystalline cellulose (secondary settlings) and lie in a range of from 40 to 160 $\mu$m in granular diameter.

The aforementioned granules of crystalline cellulose are formed by granulating crystalline cellulose with water.

A caries-removing apparatus comprising a pressure tank, a mixer, and an ejection nozzle can eject the caries-removing material stably and so this apparatus is adapted for the caries-removing material. The pressure tank is loaded with grinding granules. The mixer is mounted at the bottom of the pressure tank and provided with an orifice for introducing the grinding granules. The ejection nozzle is connected with the exit of the mixer. A gas under pressure is supplied from a pressure gas source to the mixer through the pressure tank.

Selecting the diameter of the nozzle from a range of from 0.5 to 1 mm is desirable in removing caries formed in a narrow region.

The caries-removing material in accordance with the present invention uses grinding granules consisting of pulverized stones of seeds having the aforementioned certain ranges of hardnesses and granular diameters and crystalline cellulose having certain granular diameters. Therefore, the material can be ejected, along with air, from the ejection nozzle having a diameter of less than 1.0 mm. Furthermore, little pain is given to the gums during the ejection, for the following reason.

The grinding granules can be stably ejected against the caries even with a nozzle diameter of less than 1.0 mm. The granules do not directly hit the gums. If the grinding granules are reflected from the caries and from its vicinities onto the gums, the momentum of each granule is estimated to have decreased. In addition, the momentum of each individual granule is smaller than that of a granule having a greater diameter.

Only the caries can be removed without damaging the sound dentine in the same way as the caries-removing material proposed in the above-cited Japanese Patent Laid-Open No. 276292/1997, by using untoxic, pulverized stones of seeds or granules of crystalline cellulose. If the caries-removing material is left in the mouth, an unpleasant feeling is given to the patient. If he or she should swallow it, the material will not be detrimental to health.

In particular, the ejected material is so selected that it can remove the caries well but does not cut sound dentine. Only the caries can be removed simply by ejecting the material against a region including the caries. Hence, the operation is performed efficiently and accurately. Moreover, the caries-removing material is fine and light and so the material applies little heat or vibration to the teeth. When the caries are removed, little pains are induced. In addition, many of seeds that are raw materials of stones of seeds have been used as edible seeds of fruits for many years. Their safety has been established. If they are left in the mouth, little unpleasant feeling is given to the patient. The crystalline granules of cellulose is obtained by hydrolyzing refined pulp with a mineral acid to remove noncrystalline regions, refining the pulp, and drying it. Of course, the crystalline granules of cellulose are harmless to human. Since the granules contain no impurities, they are not easily contaminated with microorganisms such as molds and bacteria. Further, they can be stocked better than stones of seeds.

The caries-removing apparatus is provided with channels to permit a small amount of caries-removing material to be ejected stably. This prevents the caries-removing material from depositing in large quantity within the mouth. In consequence, little unpleasant feeling is given to the patient. Successive shots of caries removing material little interfere with each other. Therefore, the amount of caries removing material used can be saved. Additionally, caries can be removed efficiently. Moreover, ejection can be repetitively performed at short intervals of time stably.

More specifically, in the caries-removing apparatus in accordance with the present invention, the gas under pressure to be blown into the mixer can be supplied via the pressure tank. Therefore, if the orifice is made small, the gas inside the pressure tank moves into the mixer through the pipe connecting the pressure tank and the mixer and settles quickly. This feature is desirable for the repetitive operation for removing caries as described above.

The fundamental structure of the prior art blasting apparatus is disclosed, for example, in Japanese Utility Model Laid-Open No. 137390/1978. In this structure, a pressure gas source and a pressure tank are connected by a first channel. A second channel branches off from the first channel and is connected to a mixer. In this apparatus, if an orifice for introducing an ejected material into the mixer is made small to adjust the amount of ejection to a small flow rate, the flow rate of the gas from the pressure tank into the mixer is excessively limited. The pressure inside the pressure tank varies for a time after the start of the ejection. Concomitantly, the rate of ejection varies and is not stable.

DESCRIPTION OF THE PREFERRED EMBODIMENTS

Figure 1:
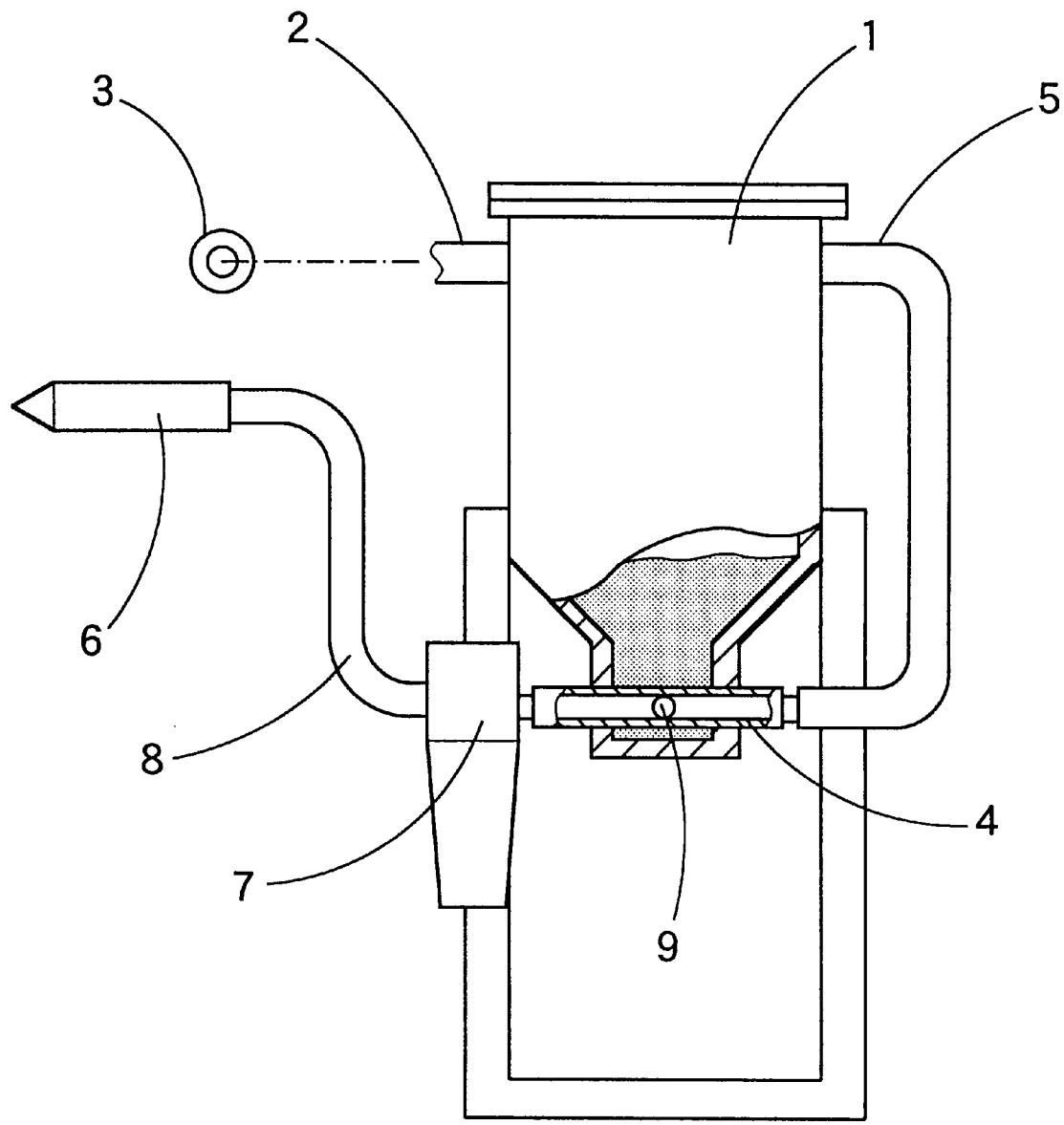
FIG. 1 is a partially cutaway view of a caries-removing apparatus in accordance with the present invention.

Essentially, a caries-removing material in accordance with the present invention consists of grinding granules ejected against dental caries, or pathological tissue, to remove them. The manner in which the grinding granules are ejected is not limited to a specific method. This method includes ejection of gas such as air or inert gas, centrifugal ejection, and ejection of liquid such as water. Normally, the material is ejected together with a gas under pressure.

One example of the caries-removing material in accordance with the invention is based on the configuration described above and characterized in that the grinding granules are pulverized, untoxic stones of seeds and that their Vickers hardness (JIS Z 1051) is in the range of from 10 to 60 Hv, preferably from 15 to 45 Hv. The granular diameters are in the range of from 40 to 160 $\mu$m, preferably from 44 to 150 $\mu$m, more preferably from 44 to 106 $\mu$m.

No limitations are placed on the aforementioned untoxic stones of seeds as long as within the range of hardness values described above. They can be stones of rosaceous seeds such as peach, plum, apricot, and Japanese apricot. Furthermore, they can be nuts such as walnut, pistachio, and almond. In addition, they can be skins of chestnuts. In addition, they can be stones of hard fruits such as acorn. Among them, stones of rosaceous seeds are especially easily and cheaply available as wastes from the food industry as mentioned above. Furthermore, then can grind caries well. In addition, almost of them are seeds of fruits having long history as foods. Their safety has been established. Therefore, use of them is desirable.

The stones of the seeds are pulverized by conventional pulverizing means. Usually, they are pulverized into sizes less than #100 with a pulverizer. Where the stones of seeds are more than 1 cm thick, they are crushed with an intermediate mill such as a crusher. Then, they are pulverized with a pulverizer, which can be a ball mill, tube mill, rod mill, roller mill, or the like.

The Vickers hardness (JIS Z 1051) was determined by placing a load of 15 g in accordance with JIS Z 1051, leaving the condition as it is for 5 seconds, and measuring the resulting impression. Materials having hardness values exceeding 60 Hv cannot be easily obtained from stones of seeds. Furthermore, they are too hard and so if they are left inside the mouth, a great feeling of wrongness is given to the patient. That is, the patient easily feels uncomfortable. On the other hand, with materials having hardness values of less than 10 Hv, it is difficult to remove caries sufficiently.

Where the diameters of the grinding granules are in excess of 160 μm, if they hit the gums during ejection of air, the patient often feels a pain. Where the diameters are 106 μm or less, the patient feels almost no pain. With the diameters less than 40 μm, the caries cannot be sufficiently removed. In addition, the patient often feels dusty during ejection of air (see Table 3 of testing examples).

The pulverized material in the above-described ranges is prepared by grading pulverized material with a general-purpose grader using micromesh (testing mesh) specified by JIS Z 8801, for example.

A further caries-removing material in accordance with the present invention consists of grinding granules that are crystalline cellulose (secondary settlings) and lie in a range of from 40 to 160 μm in granular diameter. The granules of the crystalline cellulose are secondary settlings formed by granulating crystalline cellulose. The crystalline cellulose is also known as microcrystalline cellulose and prepared by hydrolyzing refined pulp with a mineral acid to remove noncrystalline regions, refining the pulp, and drying it. Since the granules of the crystalline cellulose are, of course, untoxic and contain no impurities, they are not easily contaminated with microorganisms such as molds and bacteria. Further, they can be easily stocked. In addition, granules of uniform size can be easily manufactured. They are adapted for stable grinding granules to be ejected.

Where the granules of the crystalline cellulose are deformed, less reflections occur inside the mouth with desirable results. The granules may also be spherical.

The granular size of the grinding granules are set to the above-described range in the same way as in the case of caries-removing material. Of course, the hardness of the granules of the crystalline cellulose is higher than the hardness of the boundary between the caries and the sound dentine and lower than the hardness of the sound dentine. That is, the hardness, specified in terms of Vickers hardness Hv, is in the range of from 10 to 60, in the same manner as the foregoing.

With grinding granules having hardness values less than the range described above, it is difficult to remove caries completely. At hardness values greater than the range described above, if the material is left in the mouth, a great feeling of wrongness is given to the patient. Furthermore, there is a possibility of removing even the sound dentine.

Examples of the granules of cellulose satisfying the requirements described above include Celfia CP-102, CP-203, Abicell PH102 (granular sizes of 80 to 120 μm), and PH302 (120 to 150 μm) (manufactured by Asahi Chemical Industry Co., Ltd., Japan). They can be appropriately graded before use.

A method of removing dental caries by air blasting using the caries-removing material described above is next described. A preferred example of a caries-removing apparatus adapted for the caries-removing method is shown in FIG. 1.

This apparatus essentially consists of a pressure tank 1 loaded with grinding granules P, a mixer 4 mounted at the bottom of the tank 1 and provided with an orifice 9 for entering the grinding granules, and an ejection nozzle 6 connected to the exit of the mixer 4. A gas under pressure is supplied from a pressure gas source 3 into the mixer 4 via the pressure tank 1.

Specifically, the pressure tank 1 is connected with the pressure gas source 3 (such as a compressor) by a first channel 2. The gas source 3 is mounted in an assistant's unit, for example, within a dental clinic. The mixer 4 is located near the bottom of the pressure tank 1. The mixer 4 is connected with the pressure tank 1 by a second channel 5. The mixer 4 and the ejection nozzle 6 are connected via a third channel 8 and an ejection control valve 7. The orifice 9 in communication with the interior of the pressure tank 1 is formed in a side surface of the mixer 4. The diameter of the orifice 9 limits the upper limit of the flow rate of ejection. In the illustrated example, the ejection control valve 7 can be a solenoid valve that can be opened and closed by a foot switch and an electric circuit (none of which are shown).

In this caries-removing apparatus, the pressure tank 1 is filled with a gas under pressure by loading the caries-removing material into the pressure tank 1 and supplying the gas from the pressure gas source 3. Then, the ejection nozzle 6 is directed toward the caries. Under this condition, the foot switch (not shown) is operated to open the ejection control valve 7. The gas in the pressure tank 1 is forced into the mixer 4 through the second channel 5. The gas passes through the third channel 8, together with the caries-removing material entered from the orifice 9. The gas is emitted at high speed toward the caries from the ejection nozzle 6. Thus, the caries can be selectively removed.

The flow of the ejected gas creates a pressure gradient across the section of the pipe due to fluid resistance. The pressure inside the pressure tank 1 drops to a steady pressure that is slightly lower than the pressure occurring immediately before the ejection. Since the second channel 5 is connected with the pressure tank 1, the gas inside the tank 1 is quickly forced into the mixer 4. Consequently, the pressure inside the tank 1 momentarily settles into the value under the steady state. Therefore, if the ejection is repeated at short intervals of time, stable ejection is permitted.

Preferably, the amount of the caries-removing material ejected into the mouth is minimized. However, if the amount is too small, it takes a long time to remove the caries. This in turn will give a pain to the patient. The appropriate flow rate of the caries-removing material is 2 to 20 g/min, preferably 5 to 8 g/min.

TEST EXAMPLES

Some tests were conducted to confirm the scope of the present invention. Note that examples and comparative examples of tests 1 and 2 indicate whether any one of the requirements of the present invention is in the scope of the invention and does not always indicate whether it is in the scope of the invention.

Test Example 1

Various kinds of granules are commercially available as general-purpose ejected materials and given in Table 1. The Vickers hardness values of these granules were measured with a micro Vickers hardness tester HMV-2000 manufactured by Shimadzu in accordance with JIS Z 1051. The hardness values were compared. The measuring conditions were the same as the conditions described above. The results are given in Table 1. For comparison, granules of alumina (comparative example A), granules of glass beads (comparative example B), melanin resin (comparative example C), and granules of the cores of corns (comparative example D) were prepared. Their Vickers hardness values were 2000 to 3000 Hv, 500 to 550 Hv, 150 to 200 Hv, and 7 to 20 Hv, respectively. It can be seen that the granules of examples 1–3 consisting of stones of seeds had Vickers hardness values lying in a range of from 10 to 40 Hv.

Test Example 2

The various kinds of granules whose hardness values were measured in test example 1 and CP-102 (graded to an average granular size of 106 to 160 μm) were ejected from the caries-removing apparatus constructed as described above at an ejection pressure of 44×10⁴ Pa (4.5 k gf/cm²). The ejection nozzle had a diameter of 1.5 mm. The ejection was continued for 20 seconds. The resulting impressions were measured and compared. With respect to CP-102, the surface was visually observed. The diameter of the orifice was 0.8 mm. The inside diameter of the second channel 5 was 5 mm. The results are shown in Table 2.

In example 1, the stones of seeds of peach ground a caries model to a depth of 1.6 mm but did not grind the dentine at all. In example 2, the stones of seeds of apricot ground a caries model to a depth of 1.4 mm but did not grind the dentine at all. In example 3, the stones of seeds of walnut ground a caries model to a depth of 1.4 mm but did not grind the dentine at all. In example 4, CP-102 consisting of granules of crystalline cellulose ground a caries model well but hardly ground the dentine.

In comparative example A, alumina ground a caries model and the dentine to depths of 1.2 mm and 1.7 mm, respectively. In comparative example B, glass beads ground a caries model and the dentine to depths of 0.6 mm and 0.3 mm, respectively. These comparisons reveal that the caries-removing material made of stones of seeds which are vegetable fibers permits selective removal of caries.

In comparative example C, melanin resin ground a caries model and the dentine to depths of 1.2 mm and 0.1 mm, respectively. Although the resin enables selective removal similarly to the stone of seeds, the resin gives a feeling of wrongness to the mouth. Hence, it gives an unpleasant feeling to the patient. Furthermore, it is undesirable to swallow the resin. In consequence, it cannot be used as a caries-removing material. In comparative example D, the cores of corns did not grind the dentine but ground a caries model only to a depth of 0.4 mm.

Test Example 3

Commercially available PS#60 and PS#180 that were pulverized stones of peach seeds were graded with a testing mesh manufactured by Metron Co., Ltd. Then, the granular size distribution was measured. The pulverized, graded materials in various granular size ranges were loaded into the caries-removing apparatus described above. The materials were emitted to the caries of five examinees. The presence of pains and an unpleasant feeling was examined. The ejection conditions were similar to those of example 1 except that the nozzle diameter was 0.8 mm.

The results are given in Table 3. The pulverized stones of peach seeds in accordance with the present invention could be ejected stably. An unpleasant feeling was given to none of the examinees. The caries could be removed well without giving pains to them.

TABLE 1

| No. | Material | Vickers hardness (H$_v$) |
|---|---|---|
| Examples | | |
| 1 | stones of peach seeds, #60 | 15–40 |
| 2 | stones of apricot seeds, #60 | 14–40 |
| 3 | stones of walnut seeds, #60 | 10–30 |
| 4 | CP-102 (106–212 μm)·✕· | 8–20 |
| Comparative Examples | | |
| A | almina, #180 | 2000–3000 |
| B | glass beads, #150 | 500–550 |
| C | melanin resin, #80 | 150–200 |
| D | cores of corns, #60 | 7–20 |

·✕·Sphericity: –1.2

TABLE 2

| No. | Material | grinding depth (mm) dentine | grinding depth (mm) caries model |
|---|---|---|---|
| Examples | | | |
| 1 | stones of peach seeds, #60 | 0 | 1.6 |
| 2 | stones of apricot seeds, #60 | 0 | 1.4 |
| 3 | stones of walnut seeds, #60 | 0 | 1.4 |
| 4 | CP-102 (106–160 μm) | hardly ground | ground well |
| Comparative Examples | | | |
| A | almina, #180 | 1.7 | 1.2 |
| B | glass beads, #150 | 0.3 | 0.6 |
| C | melanin resin, #80 | 0 | 1.2 |
| D | cores of corns, #60 | 0 | 0.4 |

TABLE 3

| range of granular diameters (μm) | PS#60 | PS#180 | state of injection | remarks |
|---|---|---|---|---|
| 600 (retaining) | 1% | | not ejectable | |
| 425–600 | 33% | | not ejectable | |
| 355–425 | 25% | | not ejectable | |
| 180–355 | 34% | | always pain | All examinees felt pain. |
| 150–180 | 7% | 2% | sometimes pain | Some examinees felt pain. |
| 106–150 | | 24% | seldom pain | Some examinees felt an aversion. |
| 44–106 | | 46% | no pain | No examinees felt an aversion. |
| 44 (passed) | | 28% | dusty | Cannot be easily removed. Dusty. |

What is claimed is:

1. A caries-removing material for removing dental caries consisting of pathological tissue by ejecting the caries-removing material against said caries, said caries-removing material comprising grinding granules formed by pulverizing untoxic stones of seeds, and said grinding granules having Vickers hardness values (JIS Z 1051) of 10 to 60 Hv and granular diameters of 40 to 160 μm.

2. The caries-removing material of claim 1, wherein said grinding granules have diameters lying in a range of from 44 to 150 μm.

3. The caries-removing material of claim 2, wherein said grinding granules have diameters lying in a range of from 44 to 106 μm.

4. The caries-removing material of claim 3, wherein said stones of said seeds are selected from stones of rosaceous seeds such as peach, plum, apricot, and Japanese apricot.

5. The caries-removing material of claim 1, wherein said stones of said seeds are selected from stones of rosaceous seeds such as peach, plum, apricot, and Japanese apricot.

6. The caries-removing material of claim 2, wherein said stones of said seeds are selected from stones of rosaceous seeds such as peach, plum, apricot, and Japanese apricot.

7. A caries-removing material for removing dental caries consisting of pathological tissue by ejecting the caries-removing material against said caries, said caries-removing material comprising granules of crystalline cellulose that are secondary settlings of crystalline cellulose, said granules having diameters lying in a range of from 40 to 160 μm.

8. The caries-removing material of claim 7, wherein said granules of said crystalline cellulose are obtained by granulating crystalline cellulose with water.

9. A caries-removing apparatus comprising:

a pressure tank having a bottom and loaded with a caries-removing material comprising grinding granules being formed by pulverizing untoxic stones of seeds and having Vickers hardness values (JIS Z 1051) of 10 to 60 Hv and granular diameters of 40 to 160 μm;

a mixer mounted at the bottom of said pressure tank and provided with an orifice permitting entry of the grinding granules, said mixer having an exit;

an ejection nozzle connected to the exit of said mixer; and a pressure gas source for supplying a gas under pressure into said mixer via said pressure tank.

10. The caries-removing apparatus of claim 9, wherein said ejection nozzle has an inside exit diameter of 0.5 to 1 mm.

11. The caries-removing apparatus comprising:

a pressure tank having a bottom and loaded with a caries-removing material comprising granules of crystalline cellulose that are secondary settlings of crystalline cellulose, said granules having diameters lying in a range of from 40 to 160 μm a mixer mounted at the bottom of said pressure tank and provided with an orifice permitting entry of the granules, said mixer having an exit;

an ejection nozzle connected to the exit of said mixer; and a pressure gas source for supplying a gas under pressure into said mixer via said pressure tank.

* * * * *

UNITED STATES PATENT AND TRADEMARK OFFICE
CERTIFICATE OF CORRECTION

PATENT NO. : 6,132,212

DATED : October 17, 2000

INVENTOR(S) : Shoji HORIGUCHI et al.

It is certified that error appears in the above-identified patent and that said Letters Patent is hereby corrected as shown below: <u>ON THE TITLE PAGE</u>

Item [73] Change "Sintobrator, Ltd., Tokyo-To, Japan" to -- Sintobrator, Ltd., Aichi-ken, Japan and D&D Corporation, Tokyo-To, Japan--

Signed and Sealed this

Eighth Day of May, 2001

*Attest:*

NICHOLAS P. GODICI

*Attesting Officer*     *Acting Director of the United States Patent and Trademark Office*